United States Patent [19]

Caplin

[11] Patent Number: 5,078,597
[45] Date of Patent: Jan. 7, 1992

[54] LINGUAL ATTACHMENT

[76] Inventor: Sidney N. Caplin, 15 Towl Gate La., Syosset, N.Y. 11791

[21] Appl. No.: 692,565

[22] Filed: Apr. 29, 1991

[51] Int. Cl.⁵ ............................................. A61C 3/00
[52] U.S. Cl. ........................................ 433/18; 433/9
[58] Field of Search .................. 433/8, 9, 18, 19, 21

[56] References Cited
U.S. PATENT DOCUMENTS 3,237,305  3/1966  Hegedus ................................ 433/21
3,745,653  7/1973  Cohl ...................................... 433/9
3,835,538  9/1974  Northcutt .............................. 433/9

Primary Examiner—John J. Wilson
Attorney, Agent, or Firm—William Nitkin

[57] ABSTRACT

A lingual attachment having a base, one side of which is adhered to a tooth and the other side of which is affixed to a loop attachment member formed of wire with said loop defining an aperture therein for receipt of an orthodontic attachment member, such loop extending beyond the edge of the base and curving away therefrom.

5 Claims, 2 Drawing Sheets

LINGUAL ATTACHMENT

BACKGROUND OF THE INVENTION

1. Field of the Invention

The device of this invention resides in the area of orthodontic devices and more particularly relates to lingual loops for retention of various orthodontic attachment members to a tooth.

2. Description of the Prior Art

Lingual buttons, hooks and cleats are well known in the prior art. Over the years these attachment structures have proven to lack versatility and have caused oral irritations to some patients as these devices protrude significantly from the teeth lo which they are attached. With the Increased use of ceramic brackets for aesthetic reasons, these types of buttons, hooks and cleats have been found in many cases not to provide the needed installation control. Generally lingual buttons are rounded disks mounted on a protruding shaft extending from a base which base can be flat or curved in cross-section and round to rectangular in shape. Lingual cleats usually have two arms oppositely extending from a common base while lingual hooks have one arm with side extensions (tie wings) also extending from a base. The base can include a layer such as of extra fine wire mesh usually of stainless steel or of stainless steel foil and which base can be adhered to a tooth by orthodontic bonding material such as Ormco System 1, Unitech Bond-eze or equivalent bonding material.

SUMMARY OF THE INVENTION

It is an object of this invention to provide a low-profile, non-irritating ligual loop, in two designs. The lingual loops of this invention help to eliminate patient complaints associated with prior art lingual buttons, hooks and cleats.

It is a further object of this invention to provide a strong, versatile and easy-to-place lingual loop through which elastomeric thread, ligatures or springs can be tied or attached through the loop's eyelet for orthodontic uses. The lingual loops of this invention can also be used as directional hooks and for attaching coil springs to surgically exposed teeth.

It is a yet further object of this invention that these non-irritating, low-profile loop structures provide maximum adaptation for attachment to each tooth such that they can hold attachment members from most directions whether they are occlusal, mesial, distal and the like.

It is a still further object of this invention for the device to be used in conjunction with ceramics for rotation since no metal will show when elastomeric-type threads are used The loops of this invention when applied are very strong and rotations can be started as soon as the orthodontic bonding material has set. This invention features extreme ease of placement using a college plier and the loop attachment members can be cleared easily of adhesive by using a burr if they become obstructed.

The loops of this invention are composed of a base, which can be flat or contoured to which a 0.016 inch soft wire loop is attached by welding. The wire loop is of malleable wire so that it can be bent if desired. The base is bonded to the buccal or lingual surface of a tooth by orthodontic bonding material as in the prior art. The loop members can extend gingivally but since they protrude so little and are rounded, they do not irritate the patient. The loops can also have lingual placement on cuspids as well as act like lingual hooks on premolars. The device of this invention can be utilized with cross elastics if placed on opposite sides of adjacent teeth to retract highly buccally located cuspids.

DESCRIPTION OF THE PREFERRED EMBODIMENT(S)

Figure 1:
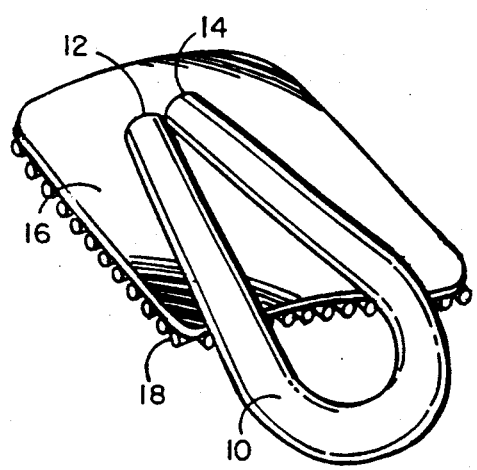
FIG. 1 illustrates a perspective view of one embodiment of the loop device of this invention.
Figure 2:
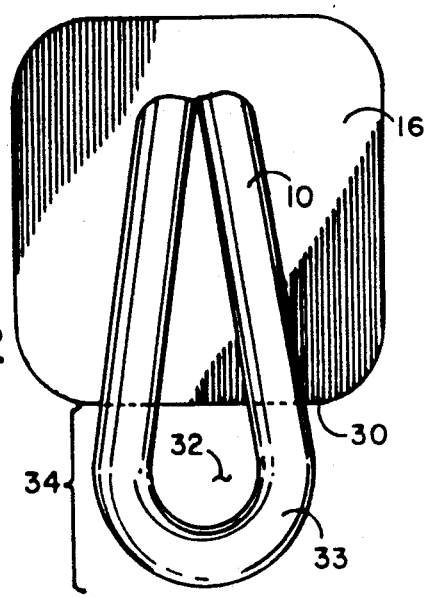
FIG. 2 illustrates a front view of the embodiment of this invention seen in FIG. 1.
Figure 3:
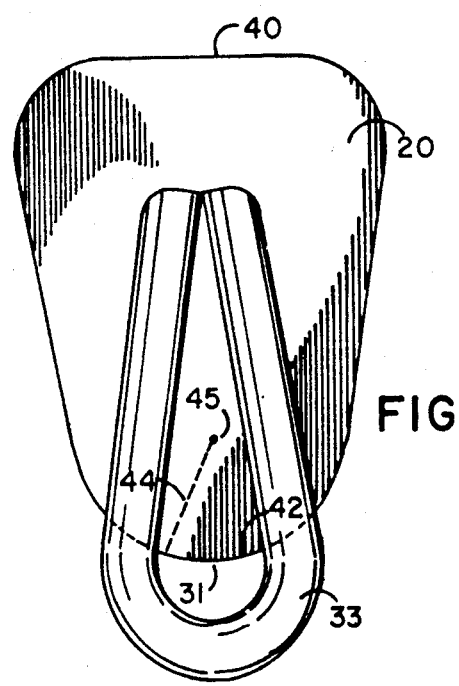
FIG. 3 illustrates a front view of an alternate embodiment of this invention from that illustrated in FIG. 2.
Figure 4:
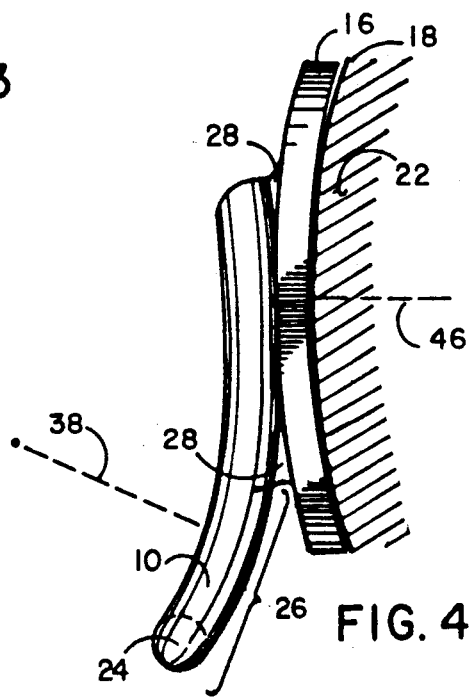
FIG. 4 illustrates a side cross-sectional view of a tooth segment showing the loop device of FIG. 2 attached thereto.
Figure 5:
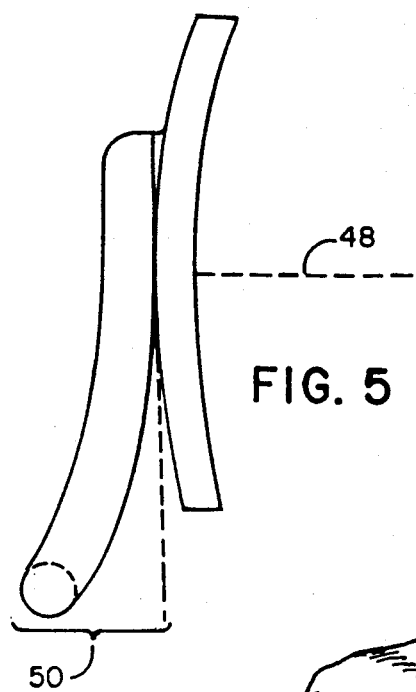
FIG. 5 illustrates a side cross-sectional view of the loop device of FIG. 3.
Figure 6:
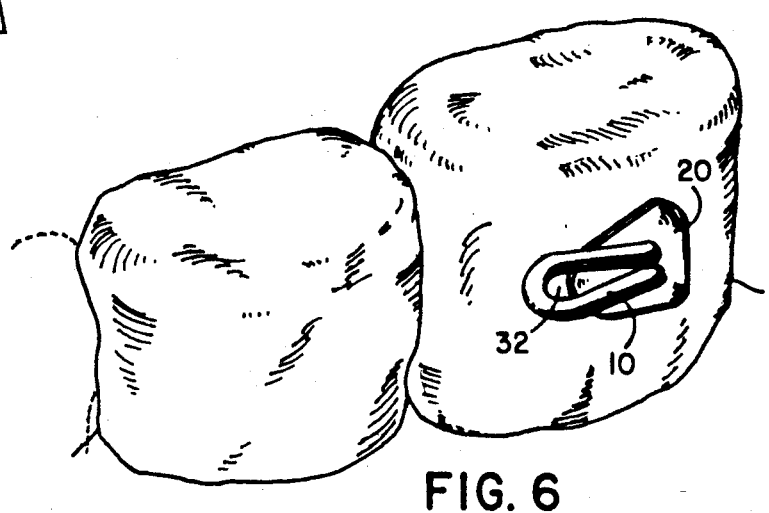
FIG. 6 illustrates a loop device of this invention bonded to a molar ready for attachment of an elastomeric thread or other attachment member.
Figure 7:
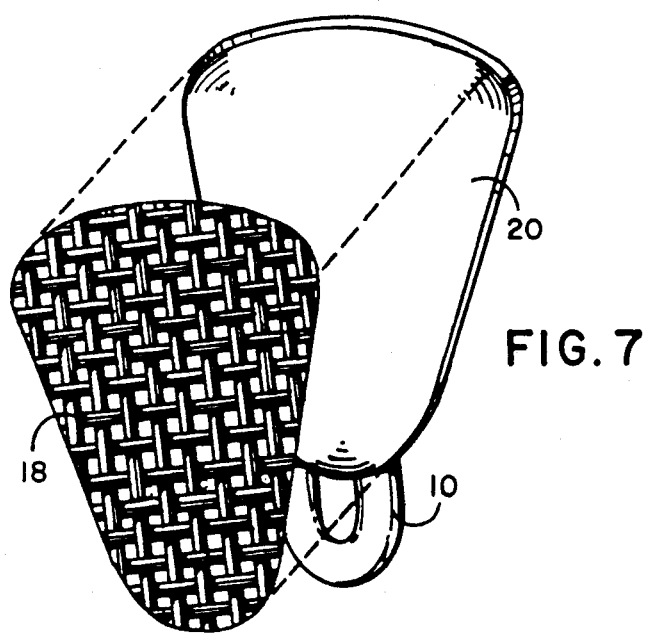
FIG. 7 illustrates a rear view of the loop device of this invention showing a base with wire mesh separated therefrom.

FIG. 1 illustrates a perspective view of one embodiment of the device of this invention showing loop member 10 which is curved back upon itself so that first end 12 contacts second end 14. Loop 10 is welded onto base member 16 to which is adhered mesh member 18. Mesh member 18 acts as a backing and helps base member 16 to be more securely adhered to a tooth. Other backings and processes can be used to impart sufficient physical properties for the bonding material to adhere to the device, such as acid etching the rear face of base member 16. As seen in FIG. 2 base member 16 can be rectangular in shape or somewhat triangular as is the shape of base 20 seen in FIG. 3: FIG. 4 illustrates a cross-sectional view of FIG. 2 through a tooth segment showing base member 16 and mesh member 18 attached to tooth 22 with loop 10 bent at its bottom 24 in the opposite direction from the direction of the curve of base member 16, leaving a large space 26 through which elastomeric thread or other attachment means can be inserted. Loop 10 can be attached to base member 16 by welding 28. FIG. 6 illustrates a loop device of this invention bonded in place with orthodontic bonding material to a molar, such device ready to receive an attachment means through aperture 32. FIG. 7 illustrates mesh member 18 separated from base 20 to be positioned thereon by adhesive, welding or any equivalent means which attachment Is done during the manufacturing process. Mesh members or their equivalent provide a base to receive and hold the orthodontic bonding material to bond the loop device to the tooth. Loop 10, as seen in FIGS. 1 and 2, is approximately 4.27 mm long and extends 1.6 mm beyond end 30 of base member 16 and 1 mm beyond the end 31 of base 20 as seen in FIG. 3 and is approximately 2 mm wide at its widest point leaving aperture 32 of approximatey 1 mm in diameter defined within the loop's protruding portion 33 extending beyond base member 16 or base 20. The loop extends a distance 50 away from base member 16, as seen in FIGS. 4 and 5 which distance 50 is approximtely 1.14 mm from its point of contact with the base, creating a space 26 therebetween through which the attachment means can pass. Extension 33 beyond bottom 30 of base member 16 or bottom 31 of base 20 is important when combined with the feature of loop 10 curving on a 4 mm radius 38 extending from a point 2.5 mm above bottom 24 of loop 10 with loop 10 curving away from base member 16 or base 20 to provide room for attachment means to be easily passed through aperture 32. In FIG. 2 base member 16 is generally square with sides 3.35 mm in length and with rounded corners. In FIG. 3 triangular base 20 is 3.3 mm at its top 40 and approximately 2 mm wide at its bottom 42 with bottom 42 rounded on a 1.25 mm radius 44 from point 45 The loop wire can have a diameter of 0.016 inch. Base member 16 and base 20 can be curved on a 3.3 mm radius 46 and 8 mm radius 48, respectively, to match tooth surfaces of various curvatures. The base can also be flatter but in all cases loop 10 must extend beyond the bottom of the base and curve away therefrom. Further the size parameters of the base and loop are important features so that the device is as small as possible but yet provides a usable attachment area for the orthodontist.

Although the present invention has been described with reference to particular embodiments, it will be apparent to those skilled in the art that variations and modifications can be substituted therefor without departing from the principles and spirit of the invention.

I claim:

1. A lingual attachment comprising:
   a base having side edges and top and bottom surfaces, said bottom surface adapted for bonding to a tooth; and
   a loop member having a first and second end, said first end attached to said top surface of said base, said loop member extending and curving around to position its second end beside said first end forming a closed loop with an aperture defined therein with the ends of said loop member affixed to the top of said base, said ends forming the top of said loop member, said curved portion of said loop defining the bottom of said loop member, said bottom of said loop member extending beyond a side edge of said base, said loop further curving away at its bottom from said base.

2. The structure of claim 1 wherein the aperture defined at the end of said loop is approximately 1 mm in diameter and the bottom of said loop curves away from said base along a radius of 4 mm from a point 2.5 mm above the bottom of said loop member.

3. The structure of claim 2 wherein said loop member is approximately 4.27 mm from top to bottom and said base member is in the range of 3.35 mm–4.3 mm in height.

4. The structure of claim 3 wherein said base member is generally rectangular in shape and said loop member extends approximately 1.6 mm beyond the bottom end thereof and the bottom of said loop member further curves away extending forward from its point of attachment to said base a distance of 1.14 mm.

5. The structure of claim 3 wherein said base member is generally triangular in shape with said loop member extending approximately 1 mm beyond the bottom end thereof and the bottom of said loop member further curves away extending forward from its point of attachment to said base a distance of 1.14 mm.

* * * * *